United States Patent [19]

Gouda et al.

[11] Patent Number: 5,668,193

[45] Date of Patent: Sep. 16, 1997

[54] SOLID SUBSTRATE COATED WITH AN AMINOPOLYSACCHARIDE

[75] Inventors: Ibrahim Gouda, Sollentuna; Olle Larm, Bromma, both of Sweden

[73] Assignee: Medicarb AB, Bromma, Sweden

[21] Appl. No.: 491,889

[22] PCT Filed: Jan. 14, 1994

[86] PCT No.: PCT/SE94/00022

§ 371 Date: Dec. 5, 1995

§ 102(e) Date: Dec. 5, 1995

[87] PCT Pub. No.: WO94/16750

PCT Pub. Date: Aug. 4, 1994

[30] Foreign Application Priority Data

Jan. 19, 1993 [SE] Sweden ................................. 9300140

[51] Int. Cl.[6] ............................... A61L 33/00; C08J 7/04
[52] U.S. Cl. .................... 523/112; 604/266; 210/500.24; 427/2.24; 427/2.27; 427/2.31; 427/2.1; 427/339; 427/419.7; 428/411.1; 428/421; 428/422; 428/423.1; 428/423.4; 428/425.3; 428/426; 428/436; 428/447; 428/448; 428/457; 428/458
[58] Field of Search .................... 604/266; 210/500.24; 427/339, 419.7, 2.24, 2.27, 2.31, 2.1; 428/411.1, 473, 421, 422, 423.1, 423.4, 425.3, 426, 436, 447, 448, 457, 458, 460, 461, 463, 501, 503, 532, 533, 534; 623/1, 66; 523/112

[56] References Cited

U.S. PATENT DOCUMENTS

| | | | |
|---|---|---|---|
| 4,326,532 | 4/1982 | Hammar | 604/266 |
| 4,419,444 | 12/1983 | Quash | 435/7 |
| 4,876,126 | 10/1989 | Takemura et al. | 428/35.7 |

FOREIGN PATENT DOCUMENTS

| | | |
|---|---|---|
| 0 051 354 | 5/1982 | European Pat. Off. . |
| 0 486 294 | 5/1992 | European Pat. Off. . |
| WO94/03530 | 2/1994 | WIPO . |

OTHER PUBLICATIONS

"A Method for Covalent Coupling of Heparin and Other Glycosaminoglycans to Substances Containing Primary Amino Groups", James Hoffman et al., *Carbohydrate Research*, 117, (1983)., pp. 328–331.

"A New Non–Thrombogenic Surface Prepared by Selective Covalent Binding of Heparin Via a Modified Reducing Terminal Residue", Olle Larm et al., *Biomaterials, Medical Devices and Artificial Organs*, 11(2&3), pp. 161–173 (1983).

*Primary Examiner*—Frederick Krass
*Attorney, Agent, or Firm*—Burns, Doane, Swecker & Mathis, L.L.P.

[57] ABSTRACT

A solid substrate, the surface of which has been modified to introduce reactive groups of a hydrophilic nature thereon, the modification being provided by a primer comprising a first polysaccharide containing as reactive groups amino and hydroxyl groups; and a process for the preparation of such solid substrate.

13 Claims, 2 Drawing Sheets

SOLID SUBSTRATE COATED WITH AN AMINOPOLYSACCHARIDE

TECHNICAL FIELD

The present invention relates to solid substrates, the surfaces of which have been modified to introduce reactive groups of a hydrophilic nature thereon. The invention also covers a method for preparing such solid substrates.

BACKGROUND OF THE INVENTION

In medicinal technology, such as technology involving medicinal equipment such as devices for implantation or apparatus exposed to living tissue, it is often desirable to make the exposed surfaces compatible with the environment. This is often done by immobilizing biologically active compounds onto the exposed surfaces. This is usually made in two steps, viz. a first step of activating the surface in question and a second step of coupling the biologically active compound to the activated surface.

In the first step residing in activation which frequently takes place by the treatment using a polymeric compound, the introduced reactive and functional groups should be attached to the substrate by strong binding thereto. In the second step residing in the coupling the binding shall also be as strong as possible. However, the biological activity of the immobilized substance must not be impaired.

As examples of techniques for the immobilization of a biologically active compound onto the surface of for example hospital equipment are the immobilization of glycoseaminoglycans (GAGs) on intraocular eye lenses, certain wound dressings, orthopedic implants etc. Such immobilization of GAGs is usually performed in two steps, namely pretreatment of the surface to make it more reactive and/or hydrophilic, and immobilization of the molecule by ionic or covalent binding. In such pretreatment procedure a reagent or primer containing reactive amino functions is adhered to the surface. This reagent can be further stabilized by the addition of a crosslinking agent, usually by a functional organic substance.

BACKGROUND ART

The primers and crosslinkers hitherto used are usually prepared from materials of a non-biological origin and are of a non-biodegradable type. Examples of reagents are polyethylen imine and tridodecylmethylammonium chloride. Further details on this immobilization techniques are found in Hoffman J. Larm O. and Sholander S., A new method for covalent coupling of heparin and other glycosaminoglycans to substances containing primary amino groups, Carbohydrate Research (1983) 117, 328; Larm O., Larsson R. and Olsson P., A new non-thrombogenic surface prepared by selective covalent binding of heparin via a modified reducing terminal residue, Biomaterials, Medical Devices and Artificial Organs (1983) 11, 161.

The present invention has for a main object to provide new techniques for modifying surfaces to enable the introduction of reactive groups of a hydrophilic nature on such surfaces.

Another object of the invention is to provide new techniques for performing such modification using substances that are of a biological origin and also are of a biodegradable type.

Yet another object of the invention is to introduce reactive amino and/or hydroxyl groups suitable for covalent binding of biologically active substances to the surfaces involved.

Still another object of the invention is to provide new techniques enabling modification of surfaces to make said surfaces more hydrophilic by the introduction of functional groups that can be used for covalent coupling of biologically active substances to such surfaces.

SUMMARY OF THE INVENTION

Accordingly, the present invention provides a solid substrate, the surface of which has been modified to introduce reactive groups of a hydrophilic nature thereon. The modification of the surface is provided by a primer comprising a first polysaccharide containing as reactive groups amino and hydroxyl groups. Thus, it has been surprisingly found that such first polysaccharide can be effectively attached to the surface of solid substrates, and a particularly preferred embodiment of the invention is constituted by said first polysaccharide being chitosan.

Chitosan consists of 1,4-β-bound D-glucosamine units. The polysaccharide is linear and the qualities differ with regard to the degree of N-acylation. In nature all amino groups are acetylated and the polysaccharide is then termed chitin. It is mainly obtained from shells of crabs and shrimps, It is preferred that chitosan has a degree of N-acylation of at most about 90%. A preferred degree of N-acylation is at most about 50% and preferably less than about 25%.

According to a preferred aspect of the invention said first polysaccharide has been stabilized by crosslinking using a periodateoxidated second polysaccharide having vicinal hydroxyl groups or amino and hydroxyl groups in a vicinal position, said polysaccharide having been subjected to a periodate oxidation to form at least one pair of dialdehyde functions.

It is preferred that said second polysaccharide used for stabilization by crosslinking is selected from polysaccharides the biodegradation products of which are nontoxic, such as D-glucose amine and D-glucose. It is particularly preferred that said second polysaccharide is selected from the group comprising chitosan, amylose and glycosaminoglycans.

The substrates having modified surfaces in accordance with the present invention are usually of a hydrophobic or inert nature, and can be selected from the group comprising polyolefins, polyurethanes, polyvinyl chloride, polystyten, silicone and polytetrafluoroethylene or from the group comprising medicinally acceptable metals and glass. Among the polymeric materials polyolefins are preferred, such as polyethylene or polypropylene.

The invention also provides for a process for the preparation of a solid substrate, the surface of which has been modified to introduce reactive groups of a hydrophilic nature thereon. Said process involves the following steps:

a) providing a substrate, the surface of which is to be modified;

b) preparing a solution of said first polysaccharide;

c) coating said surface with the solution resulting from step b); and d) providing precipitation of said first polysaccharide on said surface resulting in modification of its properties.

In such process it is preferred to use as said first polysaccharide a chitosan.

According to a preferred embodiment of the process of the invention the solution prepared in step b) above is supplemented with a second polysaccharide having vicinal hydroxyl groups or amino and hydroxyl groups in a vicinal position, and said second polysaccharide has been subjected to a periodate oxidation to form at least one pair of aldehyde functions. The function of said second polysaccharide is to stabilize said first polysaccharide by crosslinking.

It is preferred that said second polysaccharide is selected from polysaccharides the biodegradation products of which are non-toxic, such as D-glucosamine and D-glucose. Among particularly preferred polysaccharides constituting said second polysaccharide are chitosan, amylose and glycoseaminoglycans.

The present invention will now be further illustrated by non-limiting examples with reference to the appended drawings, wherein:

BRIEF DESCRIPTION OF THE FIGURES

FIG. 3 illustrates a number of reactions that can be used in association with the present invention in order to covalently bind biologically active substances to substrates containing amino and/or hydroxyl groups. The illustrated reactions are to be construed as examples only and are not intended to restrict the scope of the invention. In FIG. 3 illustrating covalent coupling to amino or hydroxyl groups, EDC is a water-soluble carbodiimide, and Z equals O or NR, R, R' and R" are organic groups, optionally immobilized.

Figure 1:
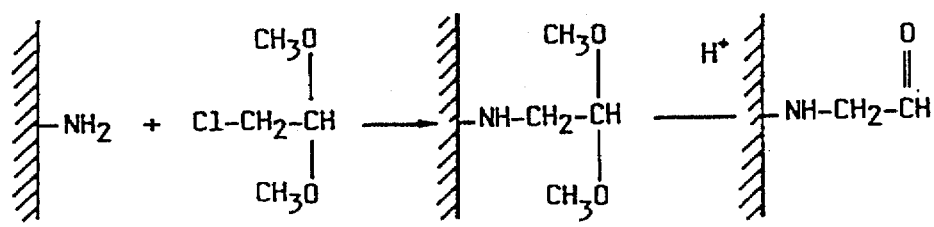
FIGS. 1 and 2 illustrate by chemical formulae a covalent coupling of carbonic anhydrase onto a surface containing primary amino groups.

In regard to substrates constituted by polymers of a hydrophobic nature, such as polyethylene and polypropylene, it is preferred to etch the surface before applying the first polysaccharide. Such etching can be performed using an oxidizing agent in acid solution, such as potassium permanganate in sulfuric acid. Such etching improves adherence of the first polysaccharide, whether stabilized by crosslinking or not.

In the non-limiting examples below percentages and parts refer to weight unless otherwise indicated.

EXAMPLE 1

Etching of polyethylene surfaces

Polyethylene film or tubing is incubated for 2 min, at room temperature with a solution of 2% potassium permanganate ($KMnO_4$) (w/v) in concentrated sulfuric acid $H_2SO_4$ and carefully rinsed with distilled water.

EXAMPLE 2

Periodate oxidation of chitosan

In a typical example when about 10% of the monosaccharide residues are oxidized the polysaccharide chitosan containing 15% N-acetyl groups is dissolved in water (100 ml) and sodium periodate (0.5 g) were added. The solution is kept in the dark at room temperature for 24 hours. The reaction mixture is then dialysed against distilled water and freeze dried to give 4.1 g chitosan containing dialdehyde functions.

EXAMPLE 3

Example 2 is repeated using amylose instead of chitosan. Similar results are obtained.

EXAMPLE 4

Example 2 is repeated using hyaluronic acid instead of chitosan. Similar results are obtained.

EXAMPLE 5

Amination with chitosan and crosslinking

The surface resulting from Example 1 is treated at room temperature with a solution of chitosan containing 15% N-acetyl groups (0.25% w/v) in water, together with a crosslinking agent (0.015% w/v) prepared as described in Example 2 above. The surface is carefully rinsed with ethanol (80%) and then stabilized by reaction for 2 hours at 50° C. with sodium cyanoborohydride (0.00025% w/v in 0.15 M NaCl, pH 3.9). The surface is rinsed with water and treated with a solution of dextran sulphate (Pharmacia AB, Uppsala Sweden)-0.1 g/L in 0.15M NaCl, pH 3.0 for 10 min at 55° C. After rinsing with large volumes of distilled water, the surface is treated with a solution of 0.25% chitosan in aqueous solution at pH 9.0, 10 min at room temperature and washed as above. The presence of amino groups is verified with an indicator (ponceau S, Sigma).

EXAMPLE 6

Example 5 is repeated but using the crosslinking agent of Example 3.

EXAMPLE 7

Example 5 is repeated but using the crosslinking agent of Example 4.

EXAMPLE 8

Amination with chitosan only.

The surface resulting from Example 1 is treated at room temperature with a solution of chitosan containing 15% N-acetyl groups (0.25% w/v) in water.

EXAMPLE 9

Covalent coupling of biologically active substance to modified surface

Polyethylene beads are etched as in Example 1 above and aminated with crosslinking as in Example 5 above. The aminated beads are further activated by treatment with a solution of borate buffer (50 ml, pH 9.0), ethanol (10 ml) and chloroacetaldehyde dimethylacetal (1 ml). To the clear solution another 40 ml of borate buffer are added and the suspension is stirred overnight at room temperature. The granulate is hydrolyzed in aqueous HCl (100 ml, 0.05M) for 25 minutes at 70° C. The reactions involved so far are illustrated in appended FIG. 1.

Figure 2:
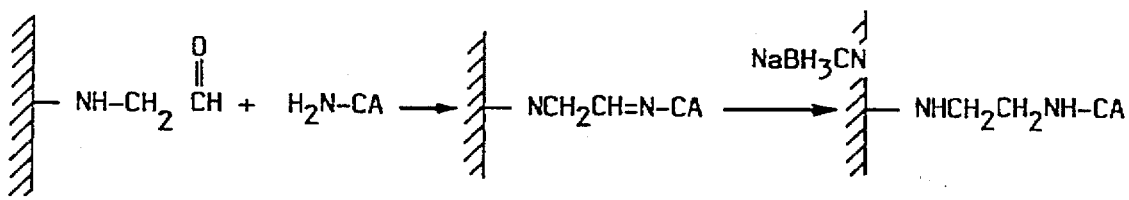
Figure 3:
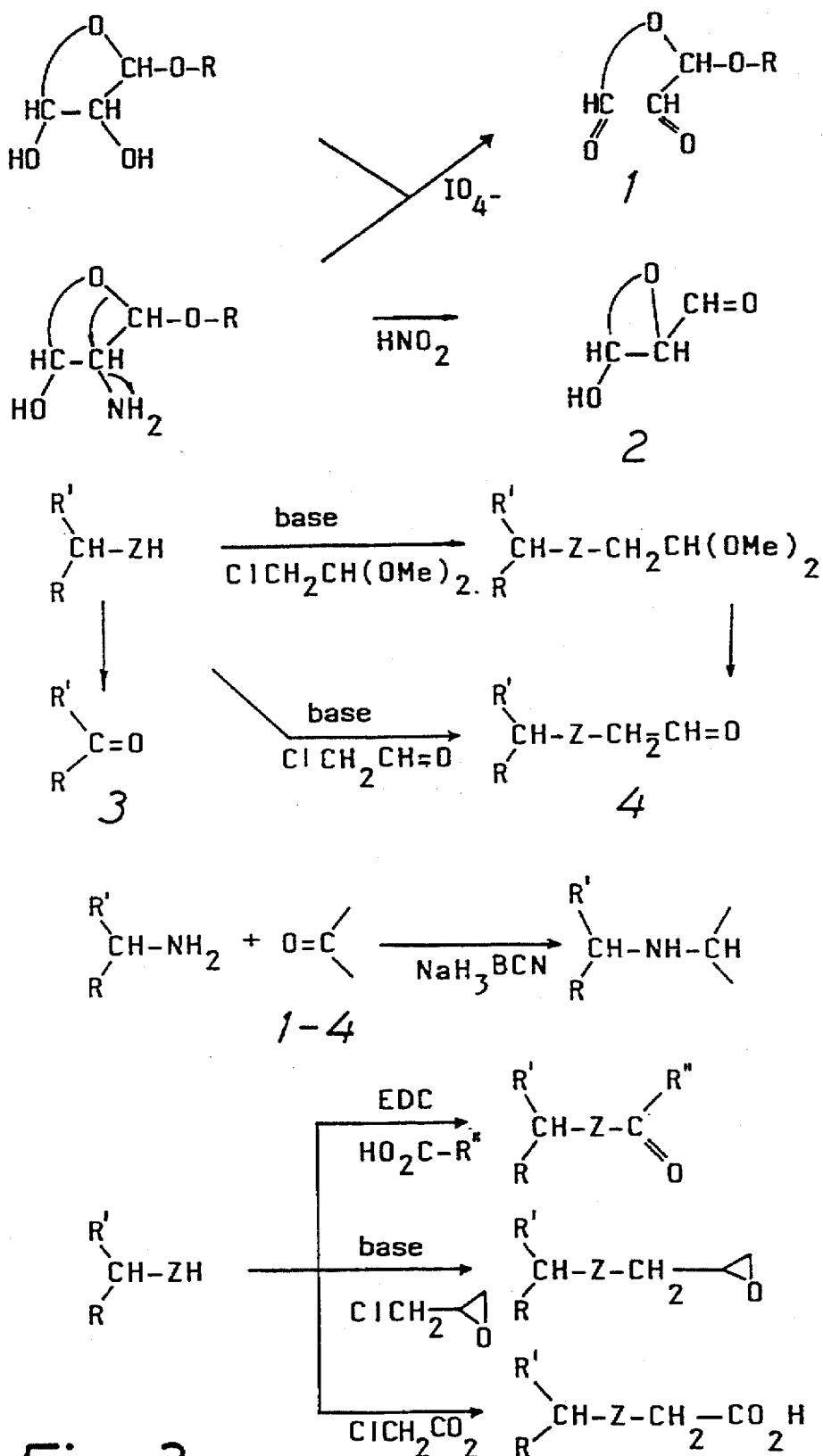
FIG. 3 is a schematic representation of conceivable coupling reactions to obtain covalent coupling of a biologically active substance to a modified substrate surface.

After washing with large volumes of water carbonic anhydrase (CA) originating from bovine erythrocytes (Sigma) is coupled by reductive amination. The granulate is stirred in an aqueous solution (200 ml, pH 6.1) containing CA (128 mg) and $NaBH_3CN$ (40 mg) at room temperature for 24 hours. This reaction is illustrated in appended FIG. 2.

After washing with water and drying the coupling yield is measured colorimetrically with respect to the ability for the immobilized enzyme to hydrolyse p-Nitrofenylacetate. The coupling yield is 5 µg/cm$^2$.

EXAMPLE 10

Carbodiimide coupling of hyaluronic acid.

Polyethylene film is etched as in Example 1 and aminated as in Example 5 and treated with a solution of hyaluronic acid (Pharmacia, 0.195 mg in 100 mL water). A solution of 1-ethyl-3-(3-dimethylaminopropyl)carbodiimide hydrochloride (EDC, Merck, 0.5 g in 1.0 mL water) is added gradually during 0.5 h. After adjustment of pH to 4.75 (0.1M HCl) the reaction is allowed to proceed over night. The films are carefully rinsed with large volumes of ultra pure water and dried. The coupling yield is 1.8 µg/cm² as determined by FTIR.

EXAMPLE 11

Immobilisation of carbonic anhydrase (CA) by carbodiimide coupling

Polyethylene beads (3 mm i diameter, 40 ml) are etched as in Example 1 and aminated as in Example 5. The beads are suspended in an aqueous solution of CA (100 ml, pH 5.5 adjusted with M HCl). EDC (2 g in 5 mL water, see Example 8) is added gradually to the stirred suspension. The pH-value is maintained at 5.5 for 24 h at room temperature. The beads are washed with large volumes of NaCl (5 L) and analysed as in Example 9. The coupling yield is 2 g/cm².

EXAMPLE 12

Carbodiimide coupling of heparansulphate

Polyethylene is etched as in Example 1 above and treated with heparansulphate (35 mg in 50 mL of water). The coupling procedure is performed as described in Example 10 with the modification that 0.2 g EDC in 1.0 mL of water is used in the coupling procedure. The coupling yield is determined semiquantatively with toluidine blue which gives a lilac colour and quantatively with FTIR (1.6 µg/cm²).

We claim:

1. A process for the preparation of a solid substrate, the surface of which has been modified to introduce hydrophilic reactive groups thereon, such modification being effected using a primer which comprises a first polysaccharide which contains reactive amino and hydroxyl groups, said process comprising the following steps:
   (a) providing a substrate, the surface of which is to be modified by the addition of hydrophilic reactive groups;
   (b) preparing a solution which contains a first polysaccharide which first polysaccharide contains reactive amino and hydroxyl groups and further contains a second polysaccharide which comprises vicinal hydroxyl groups or which contains both amino and hydroxyl groups in a vicinal position, and wherein said second polysaccharide is subjected to periodate oxidation resulting in the production of at least two dialdehyde functional groups and further resulting in the stabilization of the first polysaccharide by crosslinking;
   (c) coating said surface with the solution of step (b); and
   (d) precipitating said crosslinked first polysaccharide from said solution thereby producing a substrate which has been modified by the introduction of reactive hydrophilic groups.

2. The process of claim 1, wherein said first polysaccharide is chitosan.

3. The process of claim 2, wherein said chitosan has a degree of N-acetylation which is at most about 90%.

4. The process according to claim 3, wherein said chitosan has a degree of N-acetylation which is at most about 50%.

5. The process according to claim 4, wherein said chitosan has a degree of N-acetylation which is less than about 25%.

6. The process according to claim 1, wherein said second polysaccharide is selected from the group consisting of chitosan, amylose and glycosaminoglycans.

7. The process of claim 1, wherein the solid substrate which is modified comprises a hydrophobic solid substrate.

8. The process according to claim 1, wherein said solid substrate is selected from the group consisting of polyolefins, polyurethanes, polyvinylchloride, polystyrene, silicone and polytetrafluroethylene.

9. The process according to claim 8, wherein said polyolefin solid substrate is selected from the group consisting polyethylene and polypropylene.

10. The process according to claim 1, wherein the solid substrate which is modified comprises a medicinally acceptable metal or glass.

11. A process according to claim 1, wherein said first polysaccharide is amylose or a glycosaminoglycan.

12. A process according to claim 1, wherein step c) is preceded by an etching step to improve adhesion of said first polysaccharide to said surface, wherein said etching is performed using an oxidizing agent.

13. A process according to claim 1, wherein step c) is preceded by an etching step to improve adhesion of said first polysaccharide to said surface.

* * * * *